(12) United States Patent
Krzyzanowski

(10) Patent No.: US 6,309,404 B1
(45) Date of Patent: Oct. 30, 2001

(54) FLEXIBLE BIOPSY JAW ASSEMBLY

(76) Inventor: Jacek Krzyzanowski, 17 Oxenden Crescent, Etobicoke, Ontario (CA), M9C 4H3

( * ) Notice: Subject to any disclaimer, the term of this patent is extended or adjusted under 35 U.S.C. 154(b) by 0 days.

(21) Appl. No.: 09/420,773

(22) Filed: Oct. 19, 1999

(51) Int. Cl.$^7$ .................................................. A61B 17/28
(52) U.S. Cl. ........................................ 606/208; 606/205
(58) Field of Search ................................. 606/167, 170, 606/171, 205, 206, 207, 209; 600/562, 564, 566, 567

(56) References Cited

U.S. PATENT DOCUMENTS

| | | | |
|---|---|---|---|
| 3,895,636 | * | 7/1975 | Schmidt ................ 606/205 |
| 4,651,753 | | 3/1987 | Lifton . |
| 4,669,471 | * | 6/1987 | Hayashi ................ 606/205 |
| 4,721,116 | * | 1/1988 | Schintgen et al. ........ 606/564 |
| 4,887,612 | | 12/1989 | Esser et al. . |
| 5,133,727 | | 7/1992 | Bales et al. . |
| 5,228,451 | | 7/1993 | Bales et al. . |
| 5,238,002 | | 8/1993 | Devlin et al. . |
| 5,439,478 | | 8/1995 | Palmer . |
| 5,535,754 | | 7/1996 | Doherty . |
| 5,562,102 | | 10/1996 | Taylor et al. . |
| 5,601,585 | | 2/1997 | Banik et al. . |
| 5,681,348 | * | 10/1997 | Sato ................... 606/205 |
| 5,697,949 | | 12/1997 | Giurtino et al. . |
| 5,779,648 | | 7/1998 | Banik et al. . |
| 5,810,744 | | 9/1998 | Chu et al. . |
| 5,820,630 | | 10/1998 | Lind . |
| 5,823,971 | | 10/1998 | Robinson et al. . |
| 5,840,044 | | 4/1996 | Dassa et al. . |
| 6,074,408 | * | 6/2000 | Freeman ............... 606/205 |
| 6,083,240 | * | 7/2000 | Ouchi ................. 606/205 |
| 6,106,543 | * | 8/2000 | Esser ................. 606/205 |

FOREIGN PATENT DOCUMENTS

WO 95/08945   6/1995   (WO) .

* cited by examiner

*Primary Examiner*—Kennedy Schaetzle
*Assistant Examiner*—Kristen Droesch
(74) *Attorney, Agent, or Firm*—Eugene J. A. Gierczak

(57) ABSTRACT

A biopsy forceps device encompassing integrally designed parts for opening and closing the cutting jaws of the device and reducing the number of individual parts in the entire device and having features which specifically reduce the number of parts involved in the pivot mechanism, and having features which eliminate projections which may damage equipment used in conjunction with the device, and having features which specifically permit the device to obtain and store more than one tissue sample.

21 Claims, 11 Drawing Sheets

FLEXIBLE BIOPSY JAW ASSEMBLY

FIELD OF INVENTION

This invention relates generally to a biopsy forceps device for taking tissue samples from a patient, and more specifically to a jaw assembly for a flexible biopsy forceps device.

BACKGROUND OF INVENTION

When examining the tissues in a particular site in a patient's body, it is common for the examiner to take tissue samples from the site for analysis. This is referred to as a biopsy. A number of different biopsy devices for taking the tissue samples are in use. Typically, these biopsy devices are used in conjunction with other devices. These other devices have a lumen through which the biopsy device passes.

Some of the biopsy devices take the form of a forceps design with opposing jaws. The jaws are attached to the distal end of an elongate tube, which can be flexible or rigid. The jaws are opened and closed by an actuating mechanism. The actuating mechanism is controlled by manipulating controls located at the proximal end of the elongate tube. The actuating mechanism moves proximally and distally within the lumen of the elongate tube. This causes the jaws to rotate about an axis to cut and hold the tissue sample.

Various designs have addressed the mechanism by which the jaws pivot, and by which the actuating mechanism is attached to the jaws or to other elements which cause the jaws to open and close. These design elements combine to affect the important functional elements of the biopsy device, such as the cost of manufacture and assembly, stability, durability, ease of cleaning and sterilizing, hazards to operating personnel when cleaning and sterilizing the device or removing tissue samples, overall length of the jaw mechanism which affects the radius in which it can be passed through the bent lumen of devices used in conjunction with it, and wear or damage to the lumen of devices used in conjunction with it.

Prior art pivot mechanisms incorporate a clevis and pin, in which the pin may be a separate pin or may be an integral part of one of the jaws. Examples of biopsy devices which incorporate a clevis and integral pin may be seen with reference to U.S. Pat. No. 5,535,754 to Doherty. Examples of biopsy devices which incorporate a clevis and separate pin may be seen with reference to U.S. Pat. No. 5,238,002 to Devlin et al.

The mechanisms by which the actuating mechanism is connected to the jaws or elements, and cause jaws to open and close may be seen in reference to U.S. Pat. No. 5,133,727 to Bales et. al., U.S. Pat. No. 5,228,451 to Bales et al., U.S. Pat. No. 5,439,478 to Palmer, U.S. Pat. No. 5,238,002 to Devlin et al, U.S. Pat. No. 5,535,754 to Doherty, U.S. Pat. No. 5,820,630 to Lind and U.S. Pat. No. 4,887,612 to Esser et al.

During an examination of tissues at a site within a patient's body, the operator will want to take many samples of tissues, so as to increase the probability of obtaining tissues representative of the medical condition. When using biopsy devices that obtain and store only a single tissue sample, the device must be removed from the body, the tissue sample removed, and the biopsy device re-introduced into the patients body. The site of interest must be relocated prior to obtaining another tissue sample. This increases the time of the entire examination. The increase in time affects the cost of the procedure and risk to the patient. When the biopsy device passes through the lumen of devices used in conjunction with it, wear or damage to the lumen can occur, proportional to the number of times the biopsy device passes through the lumen.

Various designs have addressed the mechanism by which multiple tissue samples may be obtained and stored prior to removing the biopsy device from the patient. In each case the tissue sample is moved along the storage element by compression of successive samples against it, which can damage delicate tissue samples.

Examples of designs in which the sample is obtained by a side-facing cutting device or cutting knife and storage tube may be seen with reference to U.S. Pat. No. 4,651,753 to Lifton, U.S. Pat. No. 5,601,585 to Banik et al., and U.S. Pat. No. 5,810,744 to Chu et al. Examples of designs in which the sample is obtained by a means which incorporates a needle and storage tube may be seen with reference to U.S. Pat. No. 5,823,971 to Robinson et al. Examples of designs in which the sample is obtained by a set of cutting jaws, a transfixing needle and storage tube may be seen with reference to U.S. Pat. No. 5,779,648 to Banik et al., U.S. Pat. No. 5,562,102 to Taylor et al. and U.S. Pat. No. 5,840,044 to Dossa et al.

These references do not disclose a device in which elements are engaged to transport the tissue sample in the storage element so as to avoid its transport by means of compression of successive samples against it, which can damage delicate tissue samples. Nor do these references disclose a device in which the elimination of the clevis and the incorporation of a pin integral to one of the jaws are found in combination, in which the attachment of the actuating mechanism to the jaws is such so as to eliminate exposure of the ends of the actuating mechanism, and in which a flexion element is incorporated to re-open the jaw assembly.

SUMMARY OF THE INVENTION

In accordance with one aspect of the invention, a flexible biopsy jaw assembly is disclosed comprising of an enclosing means, a member having an opening and secured to the enclosing means, a sampling means pivotal within the opening about the member and an actuating member attached to the sampling means and slidable relative to the enclosing means for moving the sampling means from a closed position to an open position when activated.

In accordance with another aspect of the invention, there is provided a flexible biopsy jaw assembly further comprising of an integrally connected jaw assembly that is pivotally mounted about a flat member through an aperture located in the flat member, and actuating wires that may be attached to the integrally connected jaw assembly and may move it from a closed position to an open position.

In accordance with a further aspect of the invention, there is provided a flexible biopsy jaw assembly for removal of multiple samples of body tissue comprising of an enclosing means, a flat member having a slot means which is attached to the enclosing means, an integrally connected jaw assembly that is pivotally and slidably mounted about the flat member at the slot means, and a set of actuating wires that are attached to the jaw assembly and are slidable relative the enclosing means and move the jaw assembly from an open position to a closed position, to a flexed position.

Advantages of the present invention are: the elimination of a clevis component, therefore making the device more economical to manufacture, and easier to clean and sterilize; the elimination of the clevis also shortens the length of the jaw assembly and therefore makes it easier to negotiate the device within the endoscope which results in reducing operating time for conducting procedures, less likelihood of damaging or kinking the instrument, and less wear and tear on the endoscope; the location of the needle or pointed end of the flat member also provides improved anchoring of the device to the tissue being sampled; the orientation of the actuating wires also prevents perforation of the body tissue or organs, and tearing of the endoscope channel; the integrally connected jaws assembly eliminates the need for rivets while providing improved alignment of the jaws, improved stability when in operation, and an improved edge to edge for closing; the ability to take multiple samples of tissue with one pass of the device, therefore reducing wear and tear on the endoscope and reducing operating time for procedures.

BRIEF DESCRIPTION OF DRAWINGS

A detailed description of the preferred embodiments are provided herein below by way of example only and with reference to the following drawings, in which.

Figure 1:
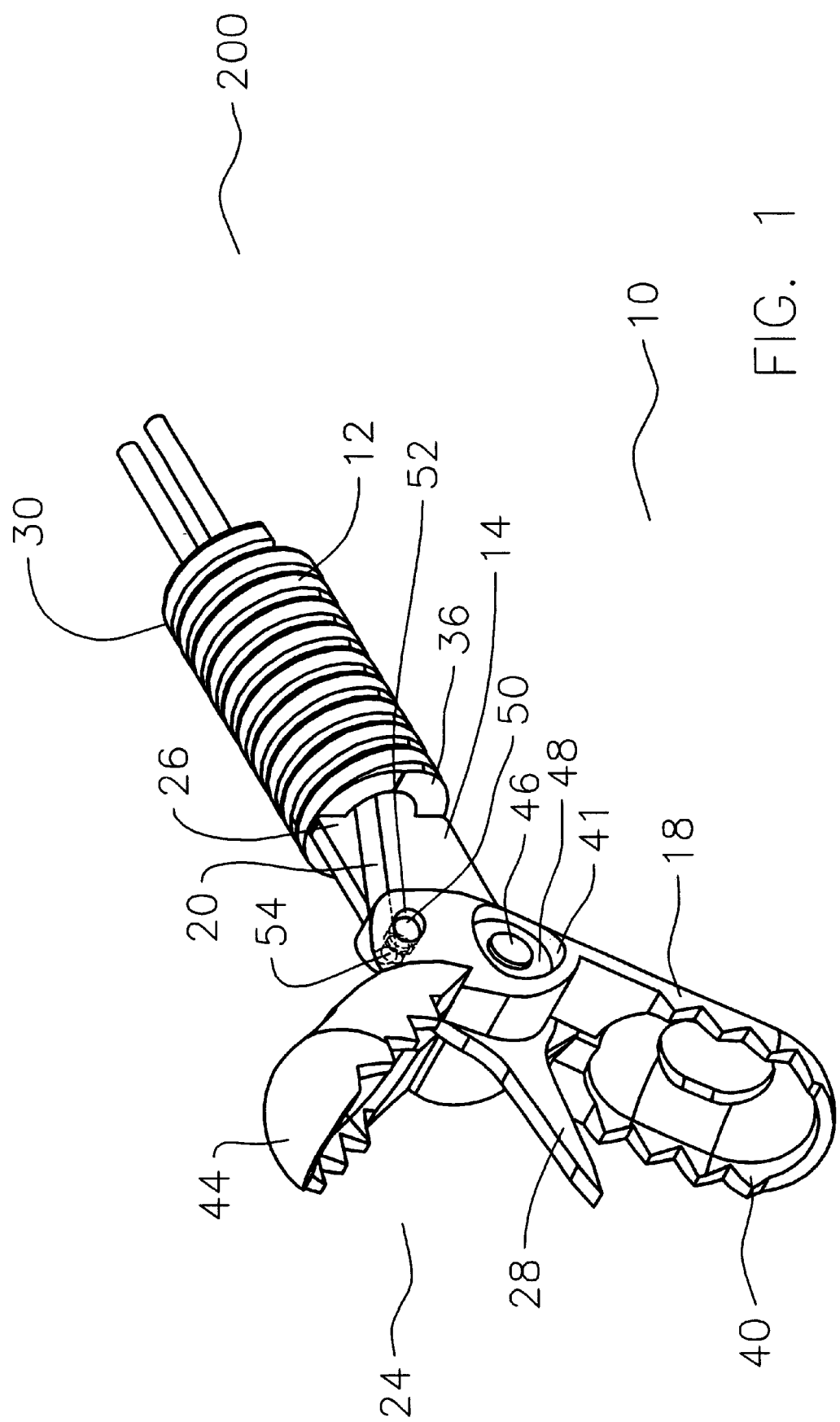
FIG. 1 is a perspective view of the flexible biopsy jaw assembly in accordance with a first preferred embodiment of the invention.
Figure 2:
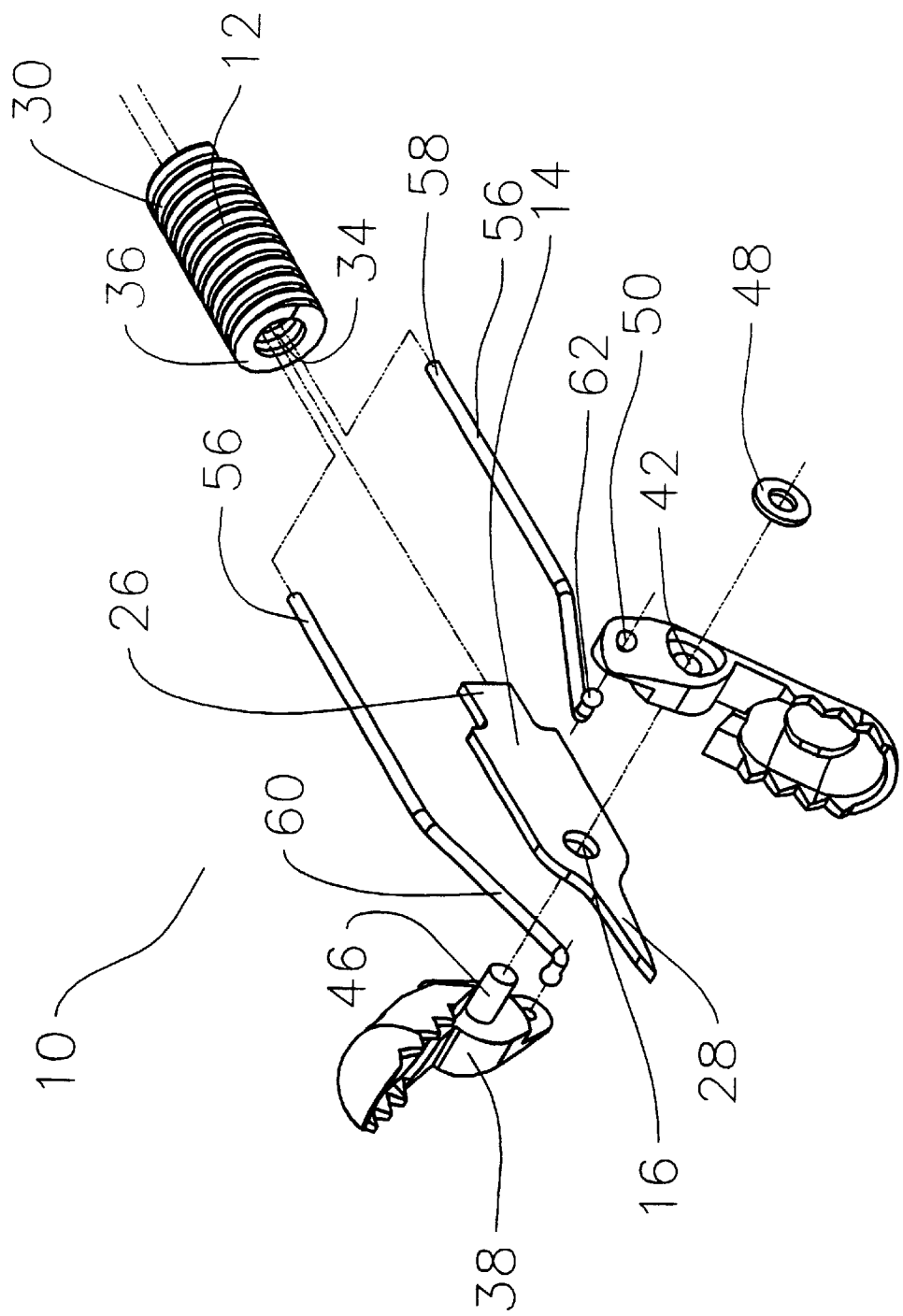
FIG. 2 is an exploded view of the flexible biopsy jaw assembly of FIG. 1.
Figure 3:
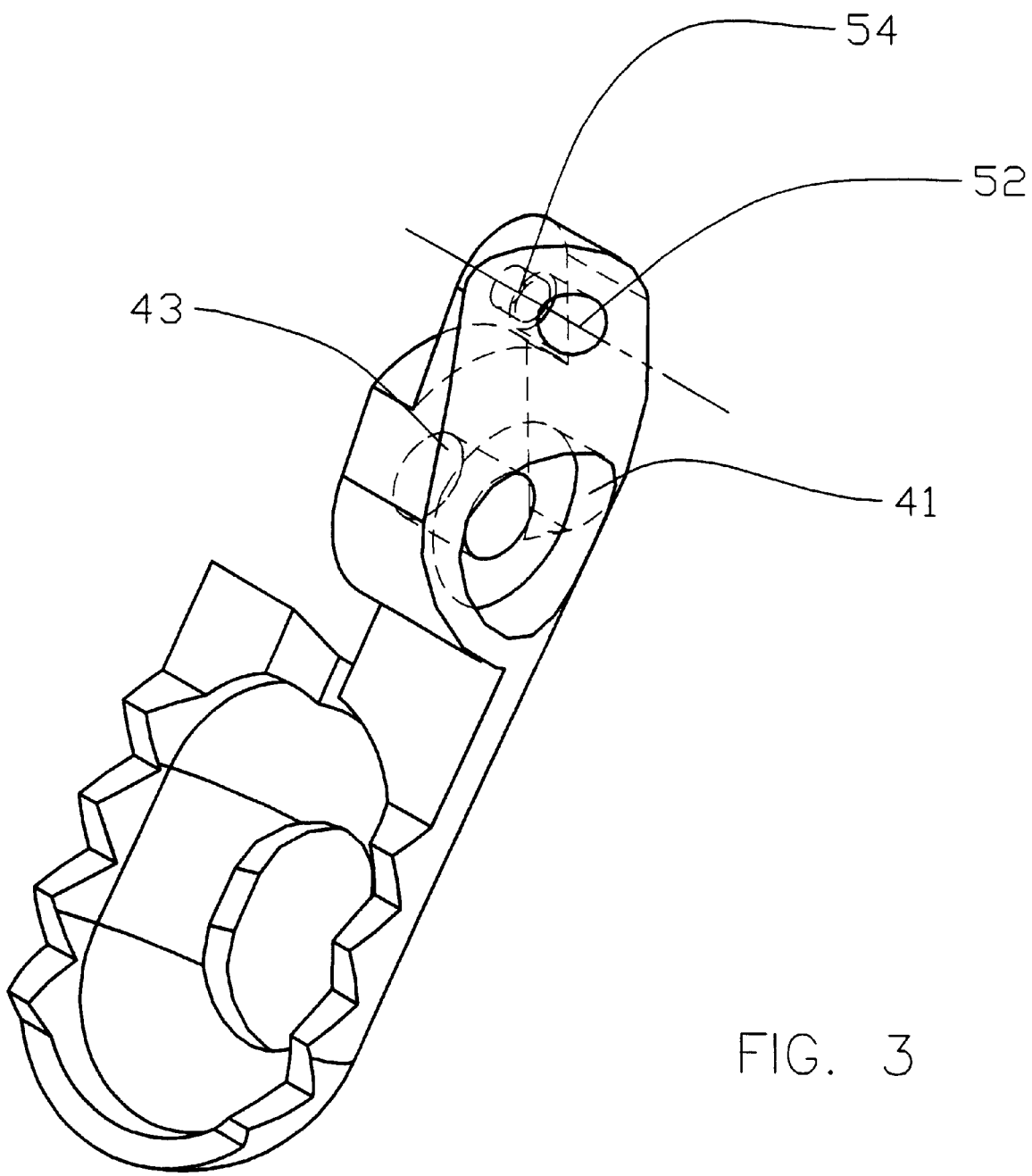
FIG. 3 is a perspective view of the flexible biopsy jaw assembly of FIG. 1 detailing the aperture and the pivot hole.
Figure 4:
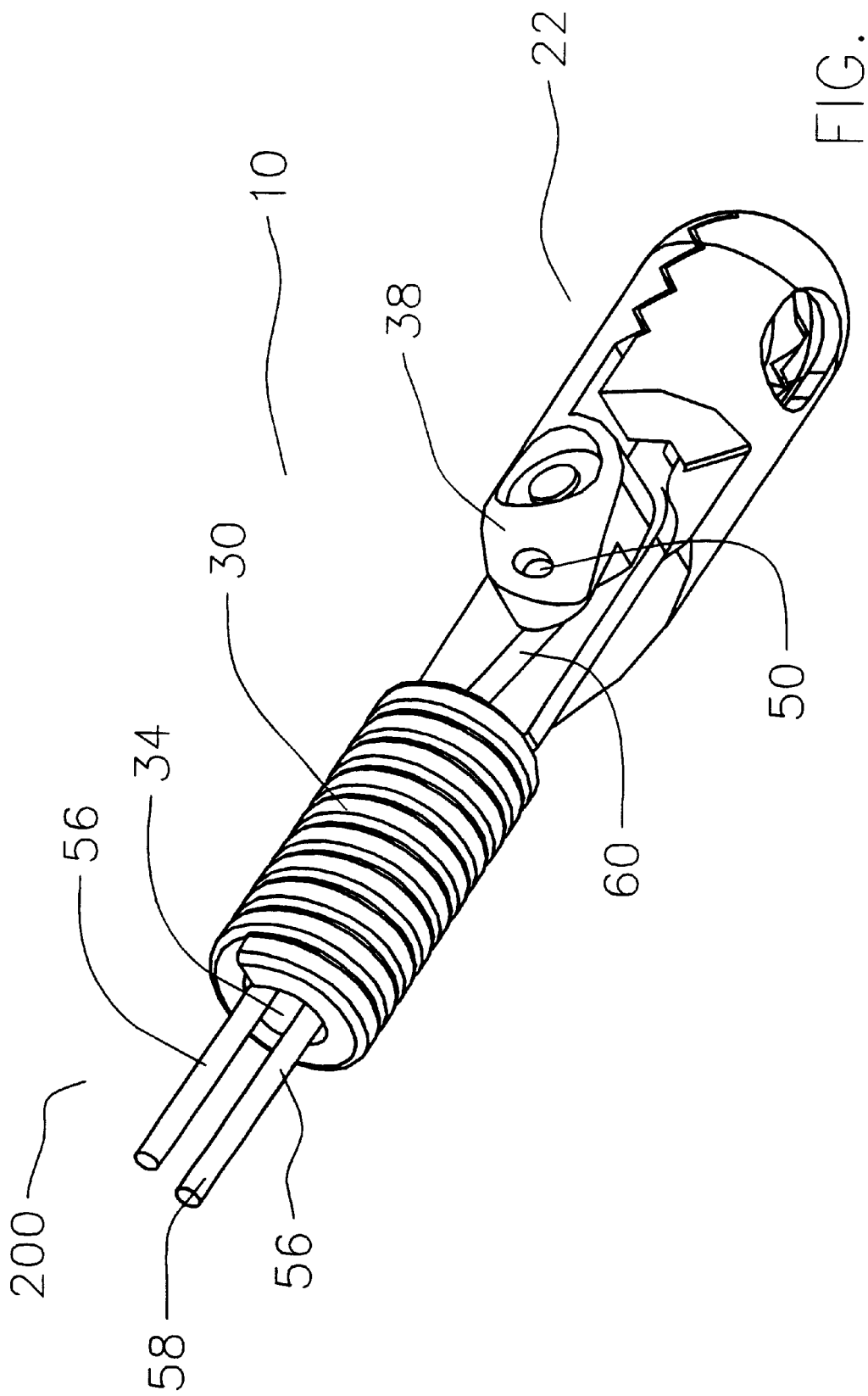
FIG. 4 is a perspective view of the flexibly biopsy jaw assembly of FIG. 1 in the closed position.

In the drawings, preferred embodiments of the invention are illustrated by way of example, It is to be expressly understood that the description and drawings are only for the purpose of illustration and as an aid to understanding and are not intended as a definition of the limits of the invention.

BEST MODE FOR CARRYING OUT THE INVENTION

In the description which follows, like parts are marked throughout the specification and the drawings with the same respective reference numerals. The drawings are not necessarily to scale and in some instances proportions may have been exaggerated in order to more clearly depict certain features of the invention.

Referring to FIGS. 1, 2, 3 and 4, there is illustrated in perspective and exploded views, a flexible biopsy jaw assembly 10 in accordance with a first preferred embodiment of the present invention. The flexible biopsy jaw assembly 10 for a biopsy forceps device 200 which may be inserted through an endoscope (not shown) for the removal of samples of body tissue from the body cavity, includes an enclosing means 12 and a member 14 having an opening 16. The member 14 may be secured to the enclosing means 12 by laser welding or welding. A sampling means 18 may be attached to the member 14 via the opening 16 whereby the sampling means 18 pivots within the opening 16 about the member 14. An actuating member 20 may be secured to the sampling means 18 and may be slidable relative the enclosing means 12 from a closed position 22 to an open position 24 when the actuating member 20 is activated.

The enclosing means 12 may be defined as either a closed coil spring 30 or a rigid structure (not shown) having a defined cavity 34 and a rim 36. The member 14 may be further defined as flat having a proximal end 26 and a distal end 28. The proximal end 26 may be secured to the rim 36 of the enclosing means 12 by welding, and the distal end 28 may be pointed or shaped like a needle so as pierce the tissue being sampled and provide stability to the assembly 10. The distal end 28 of the member 14 may also be produced without the pointed or needle end. The closed coil spring 30 allows for improved flexibility of the device 200 when inserted into endoscope, though a rigid structure (not shown) such as a rigid tube may be used as well.

The sampling means 18 may be further defined as an integrally connected jaw assembly 38 having an lower jaw 40 with a pivot hole 42 having a greater diameter 41 on one side of the pivot hole 42 and a smaller diameter 43 on the other side of the hole and an upper jaw 44 with a pin 46. In other words, the pivot hole 42 is countersunk. The lower and upper jaws, 40 and 44 respectively may be integrally connected to one another by passing the pin 46 through the opening 16 of the member 14 and into the pivot hole 42. A washer 48 may then be attached to the pin 46 that extends out of the pivot hole 42. The washer 48 may rest within the pivot hole 42 around the pin 46, as the washer 48 may pass through the pivot hole 42 with the greater diameter 41 but stop as the pivot hole 42 extends to the smaller diameter 43. Both the lower and upper jaws, 40 and 44 respectively, may be fenestrated and serrated to improve the anchorage of the assembly 10 and the preservation of the sample tissue.

Moreover, the lower jaw 40 and upper jaw 44 each include an aperture 50 whereby the aperture 50 may have a greater diameter 52 on one side of the aperture 50, and a smaller diameter 54 on the other side of the aperture 50. The actuating member 20 may be further defined as actuating wires 56 having a proximal end 58 which pass through the cavity 34 of the closed coil spring 30 and used to control the device 200 via a control mechanism or handle (not shown). The actuating wires 56 may also have a distal end 60 having a lug 62 or ball which may pass through the aperture 50 with the greater diameter 52 and rest against the smaller diameter 54. Therefore the lug 62 remains hidden within the aperture 50. Actuating wires 56 may be shaped to lie adjacent to the member 14 and within the closed coil spring 30.

In operation, the flexible biopsy jaw assembly 10 for a biopsy forceps 200 can be inserted into an endoscope (not shown) for the removal of body tissue from a body cavity. How this is achieved is explained with reference to FIG. 4. The assembly 10 may be inserted into the endoscope (not shown) via the device 200 in the closed position 22 and moved to the point where the sampling of tissue is to take place. The actuating wires 56 may be activated by the user by pushing control mechanism or handle (not shown) of the device 200. The actuating wires 56 move simultaneously through the cavity 34 relative the closed coil spring 30 which remains stationary with the member 14, thereby pushing the lower and upper jaws, 40 and 44 respectively into the open position 24.

The pointed distal end 28 of the member 14 will now be exposed and abut the tissue to be sampled. The pointed distal end 28 of the member 14 improves the anchoring of the assembly 10 on to the tissue to be sampled. When the actuating wires 56 are pulled back, the lower and upper jaws, 40 and 44 respectively, start to close and firmly grip and cut the tissue that is being held by pointed distal end 28 of the member 14. The device 200 may be removed from the endoscope (not shown) and the sample of tissue removed from the assembly 10 for examination.

Figure 5:
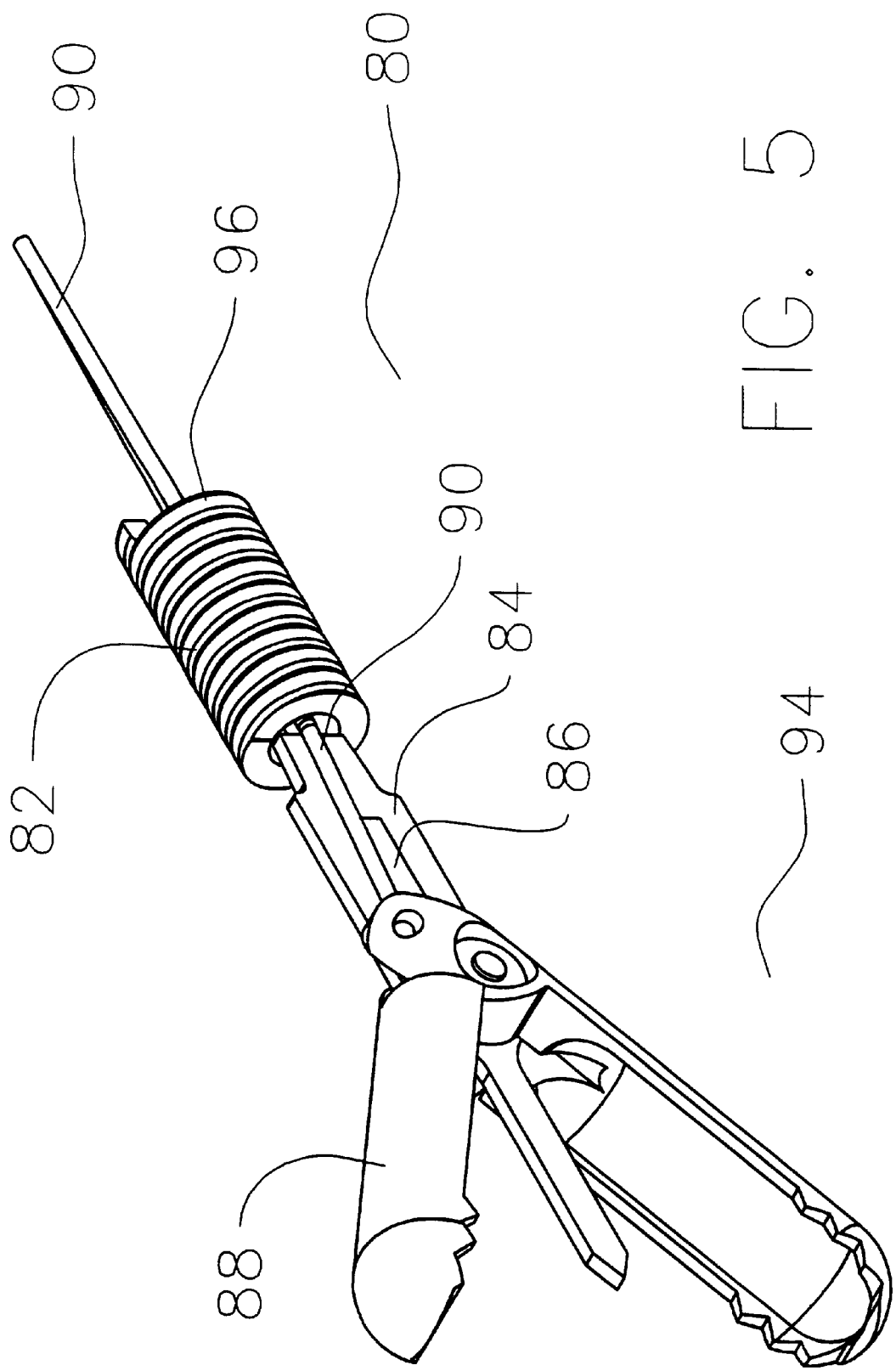
FIG. 5 is a perspective view of the flexible biopsy jaw assembly in accordance with a second preferred embodiment of the invention.
Figure 6:
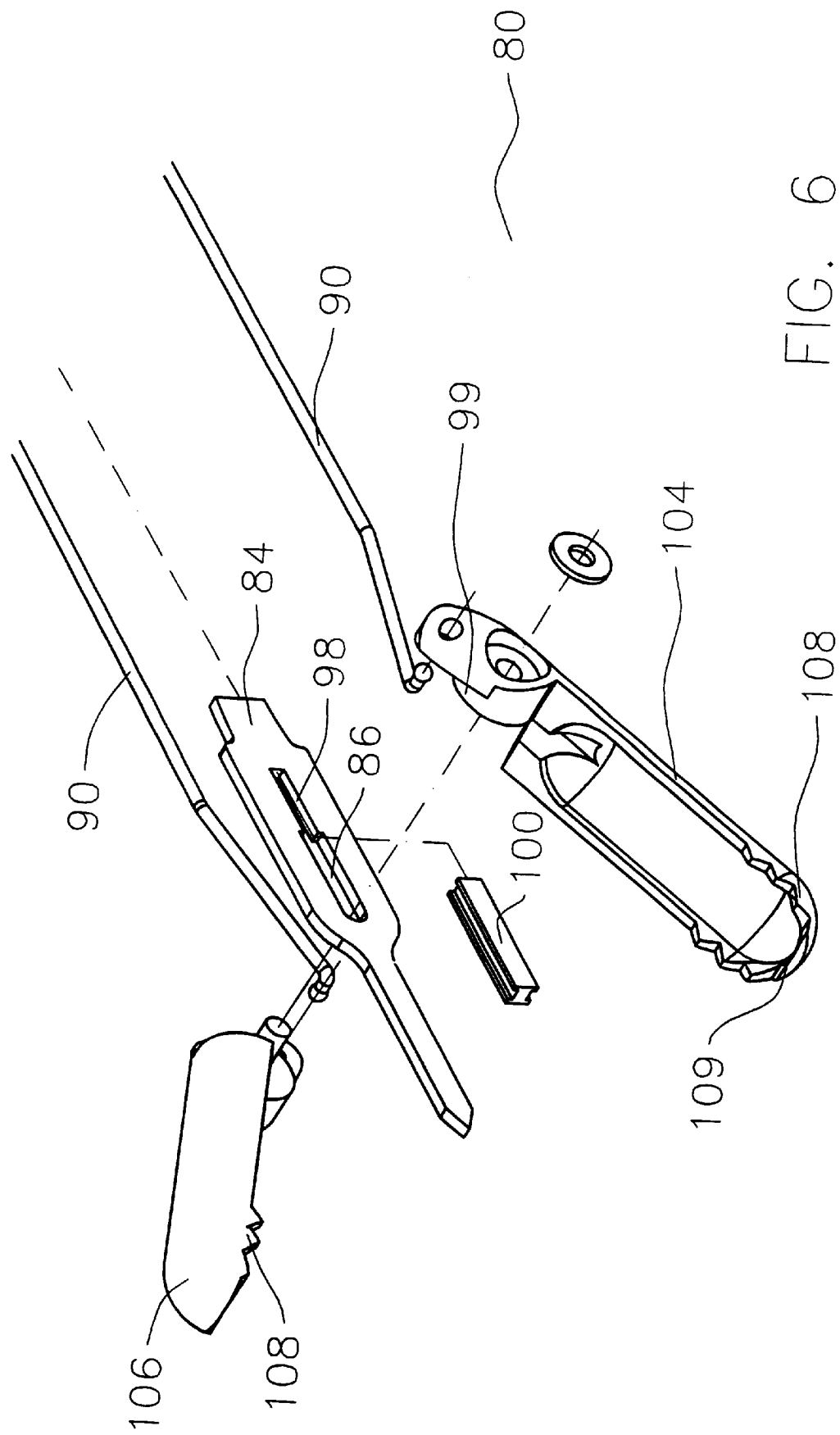
FIG. 6 is an exploded view of the flexible biopsy jaw assembly of FIG. 6.
Figure 7:
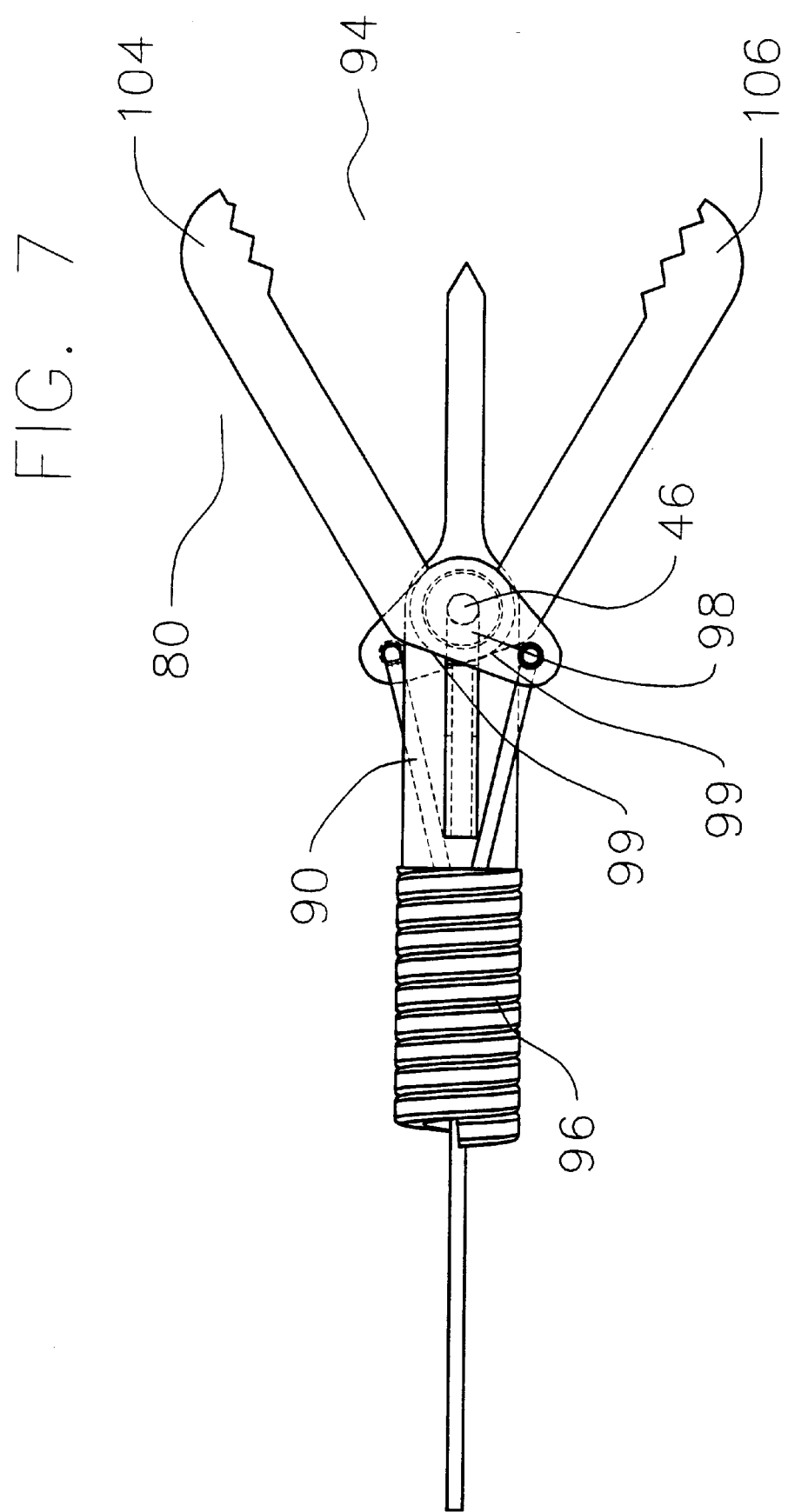
FIG. 7 is a side view of the flexibly biopsy jaw assembly of FIG. 6 in the open position.
Figure 8:
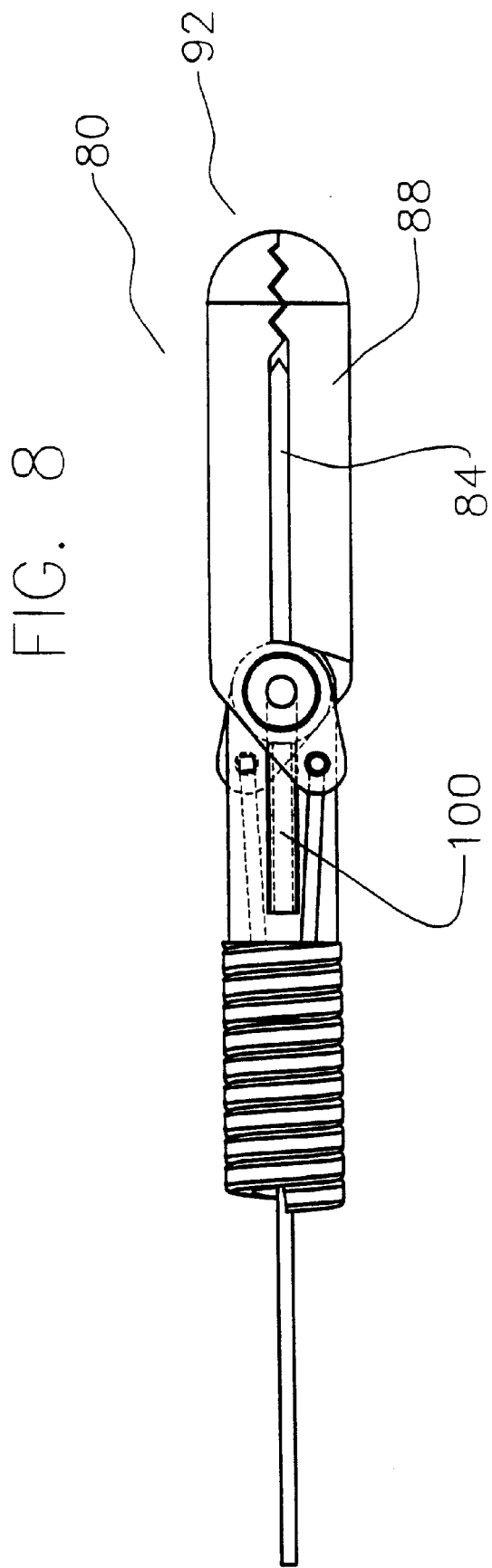
FIG. 8 is a side view of the flexible biopsy jaw assembly of FIG. 6 in the closed position.

Referring to FIGS. 5 and 6, there is illustrated in perspective and exploded views, a flexible biopsy jaw assembly 80 in accordance with a second preferred embodiment of the present invention. The flexible biopsy jaw assembly 80 for a biopsy forceps device 200 which may be inserted through an endoscope (not shown) for the removal of multiple samples of body tissue from the body cavity, includes an enclosing means 82 and a flat member 84 having an slot means 86. The flat member 84 may be secured to the enclosing means 82 by laser welding or welding. An integrally connected jaw assembly 88 may be attached to the flat member 84 via the slot means 86 whereby the integrally connected jaw assembly 88 slides and pivots within the slot means 86 about the flat member 84. Actuating wires 90 may be secured to the integrally connected jaw assembly 88 and may be slidable relative the enclosing means 82 from a closed position 92 to an open position 94 when the actuating wires 90 are activated as seen in FIG. 7 and FIG. 8.

Figure 9:
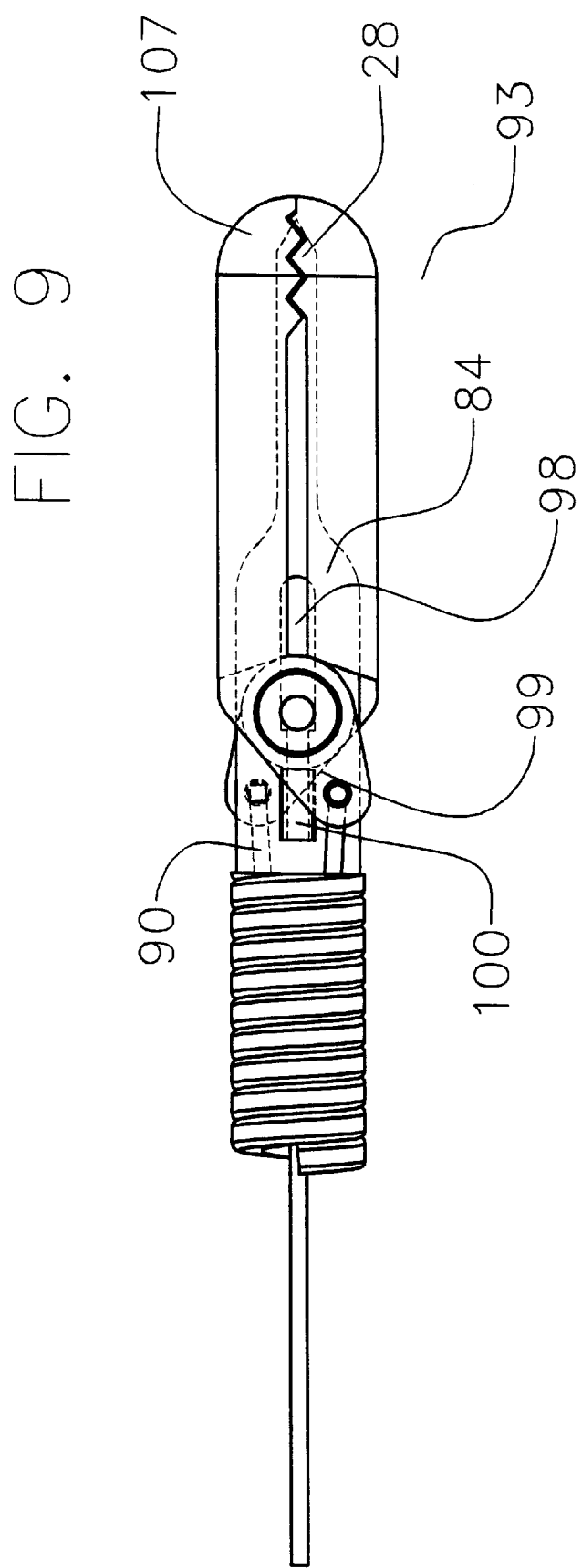
FIG. 9 is a side view of the flexibly biopsy jaw assembly of FIG. 6 in the reflexed position.
Figure 10:
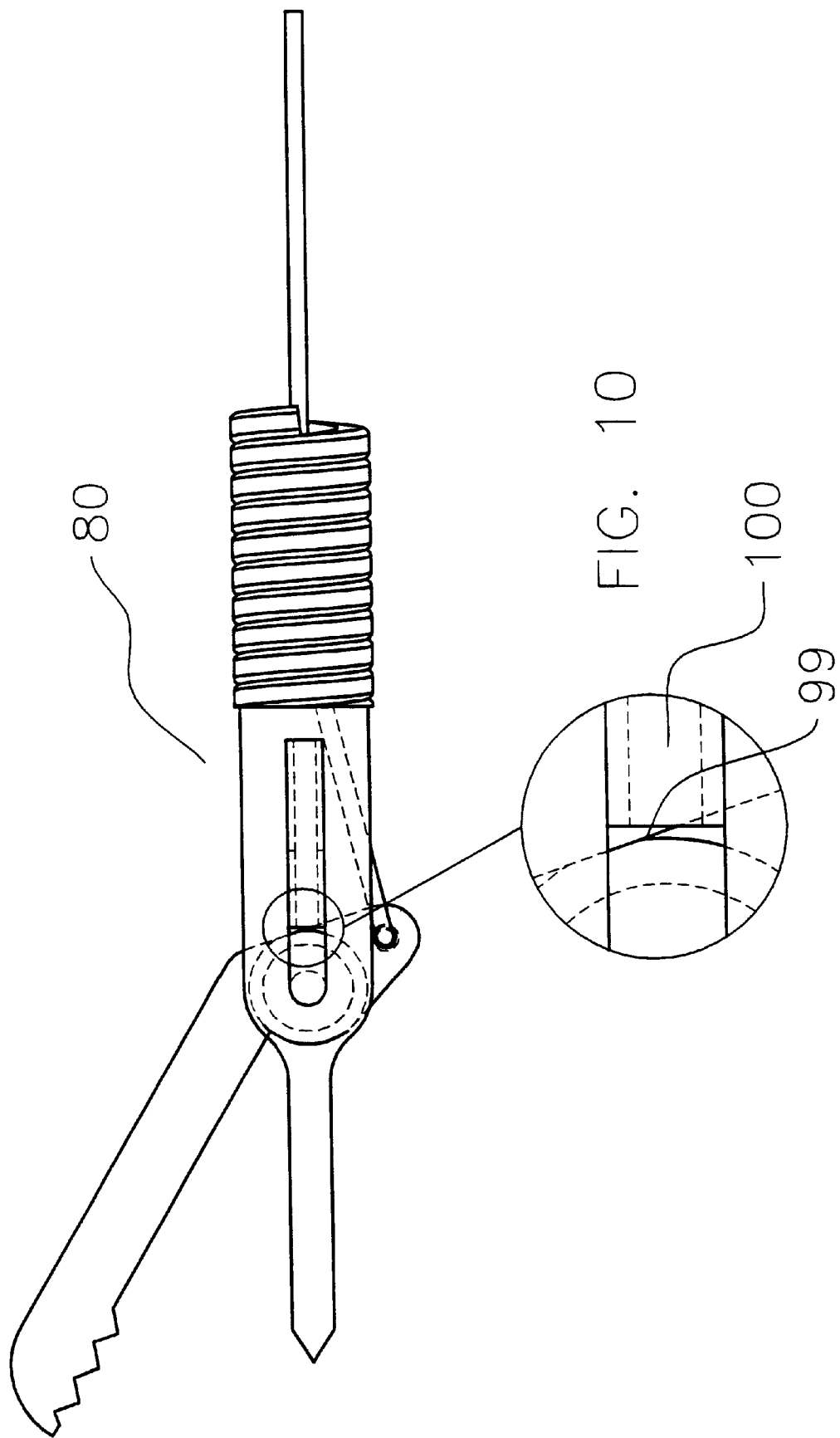
FIG. 10 is a side view of the flexible biopsy jaw assembly of FIG. 6 detailing the abutting surface against the flexion means.
Figure 11:
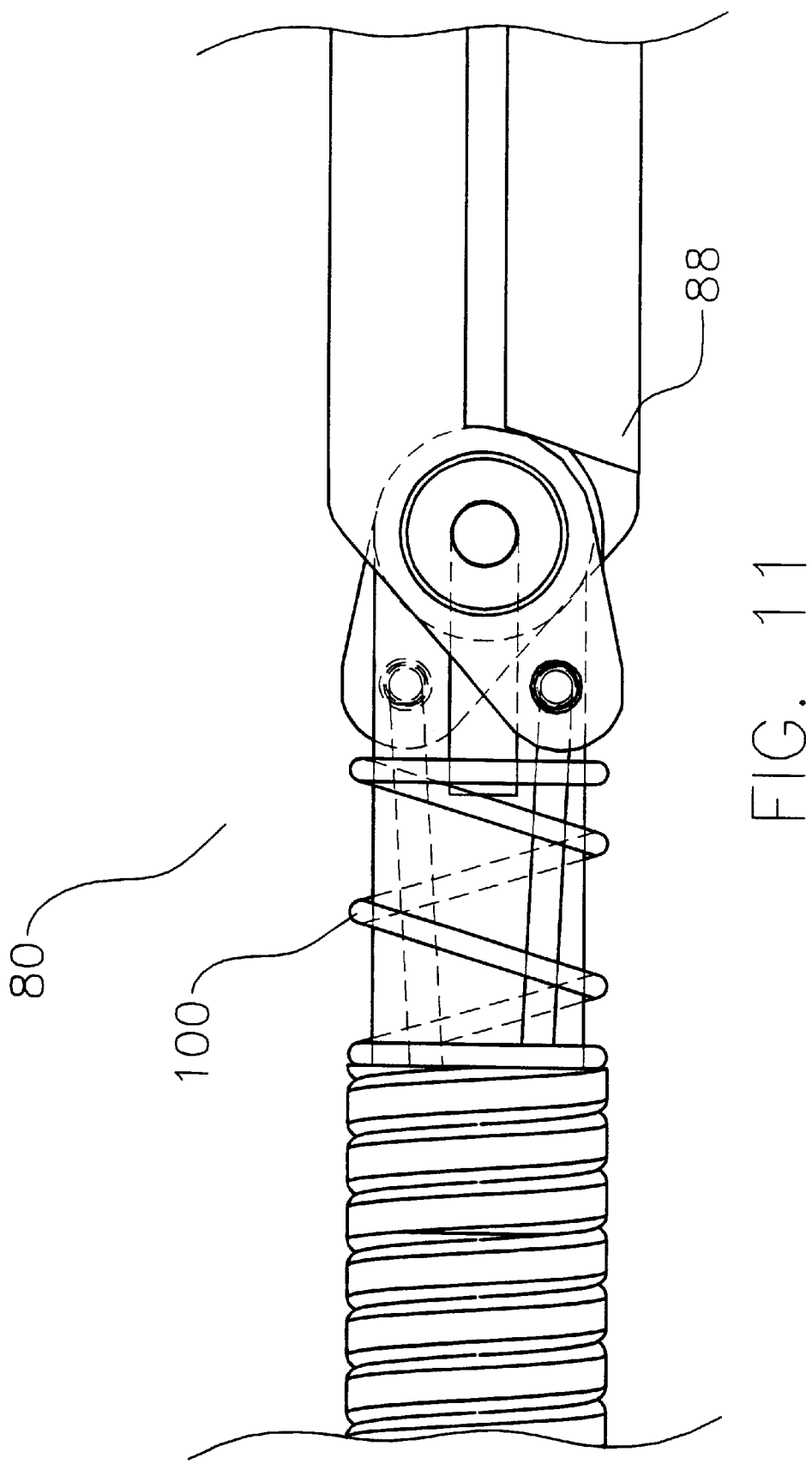
FIG. 11 is a side view of the flexible biopsy jaw assembly of FIG. 6 showing an alternative embodiment of the flexion means.

As noted above, the enclosing means 82 may be further defined as a closed coil spring 96 or a rigid structure (not shown) with features similar, if not identical to those described above for the first embodiment. The flat member 84 may include all the features described above in the first embodiment but including the slot means 86 which may be further defined as a graduated slot 98 having a flexion means 100. The integrally connected jaw assembly 88 may be further defined as having abutting surfaces 99 on both the lower and upper jaws 104 and 106 respectively, which may abut against the flexion means 100 when the flexible biopsy jaw assembly 80 is in a flexing position 93 as seem in FIG. 9. The flexion means 100 may be made from a variety of flexible materials and may be located either within the slot means 86 or associating with the closed coil spring 96 and the integrally connected jaw assembly 88 (see FIG. 11). By way of example, the flexion means 100 may have a cross-section H-shape that allows the flexion means 100 to sit securely in the graduated slot 98 without interfering with the functioning of the device 200 or the assembly 80.

The integrally connected jaw assembly 88 may be described and assembled similarly to that of the first embodiment, but with the addition that the lower and upper jaws, 104 and 106 have a serrated edge 108 whereby the serrated edges 108 mesh together when the assembly 80 is in the closed position 92. The lower and upper jaws, 104 and 106 respectively, may be further defined as having an inner surface 107 (which is within the confines of the lower and upper jaws 104 and 106). Actuating wires 90 are defined and assembled in an identical way to those described in the first embodiment.

In operation, the flexible biopsy jaw assembly 80 for a biopsy forceps 200 can be inserted into an endoscope (not shown) for the removal of multiple samples of body tissue from the body cavity. How this is achieved is explained with reference to FIGS. 7–10. The assembly 80 is activated similarly to the description for the first preferred embodiment described above. The lower and upper jaws, 104 and 106 respectively, may be anchored against the tissue in the open position 94, and start to close and firmly grip and cut the tissue when the actuating wires 90 are pulled back to the closed position 92.

As more pulling force is applied to the actuating wires 90, the integrally connected jaw assembly 88, and more specifically the pin 46 will move or slide along the graduated slot 98 therefore moving the integrally connected jaw assembly 88 relative the stationary flat member 84 to the flexing position 93. In the flexing position 93, the abutting surfaces 99 will abut against the flexion means 100 causing the flexion means 100 to flex or compress and therefore provide tension on the actuating wires 90. As the pulling force increases, the sample tissue within the integrally connected jaw assembly 88 will thread onto the pointed distal end 28 of the flat member 84 as the integrally connected jaw assembly 88 moves along the graduated slot 98.

The distance that the integrally connected jaw assembly 88 moves is relative to the length of the graduated slot 98 and the flexion of the flexion means 100, so that the pointed distal end 28 of the flat member 84 does not connect or touch the inner surface 107 of the integrally connected jaw assembly 88. This distance is important to ensure that the pointed distal end 28 of the flat member 84 does not get damaged if the pulling force is excessive. Upon release of the actuating wires 90, the flexion means 100 will flex back to a relaxed position and the integrally connected jaw assembly 88 will move from the flexed position 93 to the closed position 92. By applying a pushing force against the actuating wires 90, the assembly 80 will move towards the open position 94 and is ready to grip another sample of tissue. Therefore the assembly 80 may thread and store multiple samples of tissue on to the pointed distal end 28 of the flat member 84 without having to be removed from the endoscope (not shown) after each sample has been obtained.

Various embodiments of the invention have now been described in detail. Since changes in and/or additions to the above-described best mode may be made without departing from the nature, spirit or scope of the invention, the invention is not to be limited to said details.

I claim:

1. A flexible biopsy jaw assembly for a biopsy forceps device which may be inserted through an endoscope for the removal of body tissue from a body cavity, comprising:
    (a) a flexible tubular member;
    (b) a single flat support having a single aperture and a proximal end and a distal end wherein said proximal end is mounted directly to said flexible tubular member and said distal end is pointed;
    (c) an integrally connected jaw assembly having a cutting plane and mounted pivotally about a common axis within said single aperture for rotation of said integrally connected jaw assembly within said cutting plane of said integrally connected assembly;
    (d) a pair of actuating wires attached to said integrally connected jaw assembly and slidable relative to said flexible tubular member and said single flat support for moving said integrally connected jaw assembly from a first closed position to a second open position when activated.

2. A flexible biopsy jaw assembly as claimed in claim 1 wherein said enclosing means is further defined as a closed coil spring having a defined cavity with a rim wherein said flat member is inserted into said defined cavity and is attached to said rim.

3. A flexible biopsy jaw assembly as claimed in claim 2 wherein said integrally connected jaw assembly is defined as a lower jaw having a single tapered pivot hole and a upper jaw having a pin wherein said pin of said upper jaw passes through said aperture of said single support member and is secured to said tapered pivot hole of said lower jaw thereby hiding said pin within said tapered pivot hole.

4. A flexible biopsy jaw assembly as claimed in claim 3 wherein the securement of said pin in said tapered pivot hole is a lateral stabilizer for said upper and lower jaws.

5. A flexible biopsy jaw assembly as claimed in claim 3 wherein said lower and upper jaws each have a tapered aperture whereby one diameter of said aperture is greater in size than the second diameter of the aperture.

6. A flexible biopsy jaw assembly as claimed in claim 5 wherein said actuating wires further comprise a distal end that passes through said cavity of said closed coil spring, and a proximal end having a lug whereby said lug passes through one side of said tapered aperture and rests against the opposing side of said tapered aperature hiding said lug within said tapered aperature.

7. A flexible biopsy jaw assembly for a biopsy forceps device which may be inserted through an endoscope for the removal of multiple samples of body tissue from a body cavity, comprising:
   (a) an enclosing means;
   (b) a flat member having a slot and a proximal end and a distal end wherein said proximal end is attached to said enclosing means and said distal end is pointed;
   (c) an integrally connected jaw assembly pivotally and slidably mounted about said flat member at said slot allowing said integrally connected jaw assembly to move along said flat member and store multiple samples of body tissue;
   (d) a pair of actuating wires attached to said integrally connected jaw assembly and slidable relative said enclosing means and said flat member for moving said integrally connected jaw assembly from a first closed position to a second open position when activated.

8. A flexible biopsy jaw assembly as claimed in claim 7 wherein said flexible tubular member is further defined a closed coil spring having a defined cavity with a rim wherein said flat member is inserted into said defined cavity and is attached to said rim.

9. A flexible biopsy jaw assembly as claimed in claim 7 wherein said slot is defined as a graduated slot, and further comprising a flexion means associating with said integrally connected jaw assembly, said flexion means activating when said integrally connected jaw assembly moves between said proximal end and said distal end of said flat member.

10. A flexible biopsy jaw assembly as claimed in claim 9 wherein said integrally connected jaw assembly is defined as a lower jaw having a tapered pivot hole and a serrated edge, and a upper jaw having a pin and a serrated edge, wherein said pin of said upper jaw passes through said slot of said flat member and is secured to said tapered pivot hole of said lower jaw and said serrated edge of said lower jaw meshes with said serrated edge of said upper jaw.

11. A flexible biopsy jaw assembly as claimed in claim 10 wherein said lower and upper jaws each have a tapered aperture whereby one diameter of said aperture is greater in size than the second diameter of said aperture.

12. A flexible biopsy jaw assembly as claimed in claim 11 wherein said actuating wires further comprise a distal end that passes through said cavity of said closed coil spring, and a proximal end having a lug whereby said lug passes through one side of said tapered aperture and rests against the opposing side of said aperture.

13. A flexible biopsy jaw assembly as claimed in claim 12 wherein said actuating wires are shaped to lie adjacent to said flat member at said proximal end of said actuating wires.

14. A flexible biopsy jaw assembly for a biopsy forceps device which may be inserted through an endoscope for the removal of body tissue from a body cavity, comprising:
   (a) a closed coil spring having a defined cavity with a rim;
   (b) a flat member having a pointed distal end, a proximal end and a slot wherein said proximal end is welded to said rim of said flat member;
   (c) an integrally connected jaw assembly pivotally and slidably mounted about said flat member at said slot;
   (d) actuating wires attached to said integrally connected jaw assembly and slidable relative said closed coil spring for moving said integrally connected jaw assembly from a first closed position to a second open position when activated.

15. A flexible biopsy jaw assembly as claimed in claim 14 wherein said integrally connected jaw assembly is defined as a lower jaw having a tapered pivot hole and a serrated edge, and a upper jaw having a pin and a serrated edge, wherein said pin of said upper jaw passes through said slot means of said flat member and is secured to said tapered pivot hole of said lower jaw and said serrated edge of said lower jaw meshes with said serrated edge of said upper jaw.

16. A flexible biopsy jaw assembly as claimed in claim 15 wherein the securement of said pin in said tapered pivot hole is a lateral stabilizer for said upper and lower jaws.

17. A flexible biopsy jaw assembly as claimed in claim 15 wherein said lower and upper jaws each have a tapered aperture whereby one diameter of said aperture is greater in size than the second diameter of said aperture.

18. A flexible biopsy jaw assembly as claimed in claim 17 wherein said actuating wires further comprise a distal end that passes through said cavity of said closed coil spring, and a proximal end having a lug whereby said lug passes through one side of said tapered aperture and rests against the opposing side of said aperture.

19. A flexible biopsy jaw assembly as claimed in claim 18 wherein said actuating wires are shaped to lie adjacent to said flat member at said proximal end of said actuating wires.

20. A flexible biospy jaw assembly for a biopsy forceps device which may be inserted through an endoscope for the removal of body tissue from a body cavity, comprising:
   (a) a rigid tubular member;
   (b) a single flat support having a single aperture and a proximal end and a distal end wherein said proximal end is mounted directly to said flexible tubular member and said distal end is pointed;
   (c) an integrally connected jaw assembly having a cutting plane and mounted pivotally about a common axis within said single aperture for rotation of said integrally connected jaw assembly within said cutting plane of said integrally connected assembly;
   (d) a pair of actuating wires attached to said integrally connected jaw assembly and slidable relative to said flexible tubular member and said single flat support for moving said integrally connected jaw assembly from a first closed position to a second open position when activated.

21. A flexible biopsy jaw assembly for a biopsy forceps device which may be inserted through an endoscope for the removal of body tissue from a body cavity, comprising:
   (a) a flexible tubular member;
   (b) a single flat support having a single aperture and a proximal end and a distal end wherein said proximal end is mounted directly to said flexible tubular member;
   (c) an integrally connected jaw assembly having a cutting plane and mounted pivotally about a common axis within said single aperture for rotation of said integrally connected jaw assembly within said cutting plane of said integrally connected assembly;
   (d) a pair of actuating wires attached to said integrally connected jaw assembly and slidable relative to said flexible tubular member and said single flat support for moving said integrally connected jaw assembly from a first closed position to a second open position when activated.

* * * * *